US012125402B2

(12) United States Patent
Barash et al.

(10) Patent No.: US 12,125,402 B2
(45) Date of Patent: Oct. 22, 2024

(54) CPR COMPETITION SYSTEM

(71) Applicant: ZOLL Medical Corporation, Chelmsford, MA (US)

(72) Inventors: David Barash, Concord, MA (US); Mark Totman, Winchester, MA (US); Gary A. Freeman, Waltham, MA (US); Timothy Sean McGough, Merrimack, NH (US)

(73) Assignee: ZOLL Medical Corporation, Chelmsford, MA (US)

( * ) Notice: Subject to any disclaimer, the term of this patent is extended or adjusted under 35 U.S.C. 154(b) by 201 days.

(21) Appl. No.: 16/047,600

(22) Filed: Jul. 27, 2018

(65) Prior Publication Data
US 2018/0342179 A1 Nov. 29, 2018

Related U.S. Application Data

(63) Continuation of application No. 15/052,513, filed on Feb. 24, 2016, now Pat. No. 10,074,291, which is a
(Continued)

(51) Int. Cl.
*G09B 23/28* (2006.01)
*A63F 13/5375* (2014.01)
(Continued)

(52) U.S. Cl.
CPC ........ *G09B 23/288* (2013.01); *A63F 13/5375* (2014.09); *G09B 5/02* (2013.01); *G09B 19/003* (2013.01)

(58) Field of Classification Search
CPC ...... G09B 23/288; G09B 5/02; G09B 19/003; A63F 13/5375
See application file for complete search history.

(56) References Cited

U.S. PATENT DOCUMENTS 4,619,617 A * 10/1986 Rice ..................... G09B 19/003
434/265
4,932,879 A * 6/1990 Ingenito ............... G09B 23/288
273/454
(Continued)

FOREIGN PATENT DOCUMENTS

| CN | 101184525 A | 5/2008 |
|---|---|---|
| WO | 2009037621 A2 | 3/2009 |

OTHER PUBLICATIONS

Ribeiro et al., "Digital Integration Measuring Displacement" Mar. 1999, International Society for Optical Engineering, Conference paper in proceedings of SPIE, pp. 554-559 (Year: 1999).*
(Continued)

*Primary Examiner* — Xuan M Thai
*Assistant Examiner* — Sadaruz Zaman
(74) *Attorney, Agent, or Firm* — The Webb Law Firm

(57) ABSTRACT

A system for improving performance of chest compressions includes at least one mobile computing device, an accelerometer configured to measure a vertical displacement of a user's hands to determine information relating to rate and depth of chest compressions, and a processor; and a computer device configured to send information to and receive information from the mobile computing device(s). The system associates the information relating to the rate and depth of the chest compressions with the user; sends the information to the computer device; analyzes the information to determine a proficiency level of the user; compares the proficiency level of the user to a proficiency standard required to be certified in life saving activities; and provides an indication of whether the user of the mobile computing device is ready for certification if the proficiency level of the user meets the proficiency standard. Also, a method for certification is provided.

17 Claims, 7 Drawing Sheets

Related U.S. Application Data continuation of application No. 12/946,530, filed on Nov. 15, 2010, now abandoned.

(60) Provisional application No. 61/354,030, filed on Jun. 11, 2010, provisional application No. 61/261,274, filed on Nov. 13, 2009.

(51) Int. Cl.
*G09B 5/02* (2006.01)
*G09B 19/00* (2006.01)

(56) References Cited

U.S. PATENT DOCUMENTS

| | | | |
|---|---|---|---|
| 5,195,896 A | 3/1993 | Sweeney et al. | |
| 5,239,988 A | 8/1993 | Swanson et al. | |
| 5,496,257 A * | 3/1996 | Kelly | A61H 31/005 600/454 |
| 6,726,567 B1 | 4/2004 | Khosla | |
| 6,827,695 B2 * | 12/2004 | Palazzolo | A61B 5/721 601/41 |
| 6,921,351 B1 | 7/2005 | Hickman et al. | |
| 7,552,403 B2 * | 6/2009 | Wilson | G06F 3/038 704/275 |
| 8,262,394 B2 | 9/2012 | Walker et al. | |
| 8,734,161 B1 | 5/2014 | Centen et al. | |
| 10,074,291 B2 * | 9/2018 | Barash | G16H 20/30 |
| 10,561,575 B2 * | 2/2020 | Freeman | A61B 5/4836 |
| 10,872,537 B1 * | 12/2020 | Frist, Jr. | G16H 50/30 |
| 11,219,575 B2 * | 1/2022 | Kaufman | A61N 1/3993 |
| 2004/0157199 A1 * | 8/2004 | Eggert | G09B 23/28 434/262 |
| 2005/0058977 A1 * | 3/2005 | Cantrell | G09B 23/288 434/350 |
| 2006/0111749 A1 | 5/2006 | Westenskow et al. | |
| 2006/0173501 A1 * | 8/2006 | Stickney | A61H 31/005 607/5 |
| 2006/0285441 A1 * | 12/2006 | Walker | A61J 7/0481 368/10 |
| 2006/0292541 A1 | 12/2006 | Ehmann | |
| 2008/0171311 A1 * | 7/2008 | Centen | G16H 20/30 434/265 |
| 2008/0312565 A1 * | 12/2008 | Celik-Butler | A61H 31/005 601/43 |
| 2009/0018882 A1 | 1/2009 | Burton et al. | |
| 2009/0035733 A1 | 2/2009 | Meitar et al. | |
| 2009/0035740 A1 * | 2/2009 | Reed | G09B 23/288 434/265 |
| 2009/0148821 A1 | 6/2009 | Carkner et al. | |
| 2010/0022904 A1 | 1/2010 | Centen | |
| 2010/0271199 A1 | 10/2010 | Belov et al. | |
| 2012/0191476 A1 * | 7/2012 | Reid | G06Q 50/24 705/3 |
| 2014/0093853 A1 * | 4/2014 | Constantine, III | G09B 23/288 434/265 |
| 2015/0351647 A1 * | 12/2015 | Dantu | A61B 5/02438 601/41 |
| 2016/0256676 A1 * | 9/2016 | Freeman | A61N 1/3625 |
| 2018/0161624 A1 * | 6/2018 | Wrigg | A63B 24/0006 |
| 2018/0174489 A1 * | 6/2018 | Dellimore | A61B 5/0077 |
| 2018/0342178 A1 * | 11/2018 | Gold | A61H 31/004 |
| 2020/0349859 A1 * | 11/2020 | Shah | G06F 3/017 |
| 2021/0090450 A1 * | 3/2021 | Frist, Jr. | G16H 20/70 |
| 2021/0393479 A1 * | 12/2021 | Freeman | G09B 23/288 |
| 2022/0005369 A1 * | 1/2022 | Frist, Jr. | G16H 50/30 |
| 2022/0254278 A1 * | 8/2022 | Edney | G09B 23/288 |

OTHER PUBLICATIONS

Jensen et al., "Using e-Learning for Maintenance of ALS Competence", Resuscitation, 2009, p. 903-908, vol. 80.
Sims, "UAB Students design CPR Training for Wii game system", Jul. 20, 2009, http://blog.al.com/birmingham-news-stories//print.html?entry=/2009/07/uab_students_design_cpr_traini.html, 6 pages.

* cited by examiner

CPR COMPETITION SYSTEM

CROSS-REFERENCE TO RELATED APPLICATION

This application is a continuation of U.S. patent application Ser. No. 15/052,513 filed on Feb. 24, 2016, entitled "CPR Competition System", which is a continuation of U.S. patent application Ser. No. 12/946,530 filed on Nov. 15, 2010, entitled "CPR Competition System", which claims priority to U.S. Provisional Application Ser. No. 61/261,274, filed on Nov. 13, 2009, entitled "CPR Competition System," and U.S. Provisional Application Ser. No. 61/354,030, filed on Jun. 11, 2010, entitled "CPR Competition System," the entire contents of each of which are hereby incorporated by reference.

TECHNICAL FIELD

This document relates to computer-based systems and techniques for providing competitions between individuals and/or teams in the performance of cardiopulmonary resuscitation (CPR).

BACKGROUND

Sudden cardiac arrest (colloquially "heart attack") is a regular killer. The best treatment for cardiac arrest is quick and competent chest compressions to keep blood flowing through a victim's heart. Generally, every minute of delay in treating a cardiac arrest victim lowers the chance of survival by about ten percent. As a result, provision of CPR by people who are near the victim when the cardiac arrest begins, and until more advanced life support personnel can arrive, is crucial to survival rates for cardiac arrest.

Recognizing that critical CPR can come from lay people at the site of a cardiac arrest even more than from professional responders who may take many minutes to arrive, various organizations have promoted CPR training for lay people for decades. Such training may occur on CPR mannequins that include sensors for measuring the depth and timing of chest compressions, the timing of breathing, and the like, and with mechanisms for reporting a student's performance in a CPR cycle. Students may also practice chest compressions on foam blocks that simulate the compliance of a victim's chest, though such blocks do not provide much in the form of feedback.

Certain devices provide instruction during CPR and some could also be used in CPR training. For example, some automatic external defibrillators (AEDs) use voice commands to instruct rescuers on how to operate the units, and provide voice feedback regarding the rate and depth of chest compressions (e.g., providing a metronome for rate, and saying "push harder" or "push softer" for depth). More recently, the POCKETCPR device from Bio Detek Incorporated of Pawtucket, RI 02861, a subsidiary of ZOLL Medical Corporation, has been introduced as a small, handheld battery-operated electronic device that a rescuer may place under his or her hands during CPR to obtain similar instructions and feedback. The POCKETCPR can also be used by a student who is training for CPR. In addition, software has been developed so that controllers such as the WII MOTE for the WII viodeogaming system can provide similar feedback for people practicing CPR.

SUMMARY

This document describes technologies that involve systems and techniques that may be used to make CPR training and related lifesaving training more interesting to students, and to thereby increase the quality of the training and the number of people who want to be trained in CPR. Such techniques may also increase the amount of training and practice by each student, and may cause students to stay up-to-date in their CPR skills.

As described here, interested individuals who own computing devices that contain accelerometers of sufficient sensitivity may obtain one or more computer applications that provide CPR training and testing. The applications may be run on the computing devices and may report results of the testing to a central facility that tracks results for a large number of trainees. The central facility may coordinate training campaigns for users, by which the users are drilled in a variety of different ways and settings, so as to test their ability to perform CPR effectively and also to make the CPR training process more entertaining. For example, the CPR training may be integrated as a central component of a broader role player game, such as by a player choosing to be an army medic in a first-person shooter style war or disaster simulation game, where the player can choose to attend to injured players or avatars. Data on the player's CPR and other life-saving performances may be gathered from such games, so as to obtain indication of how the player performs under pressure and in the context of a real emergency situation. In addition, the player is much more likely to practice the CPR if it is part of a more general game that they enjoy, rather than part of a standalone, fixed game that only involves performance of CPR.

The training discussed here may also lead to certification using the same equipment. For example, after a user downloads a software application for practicing CPR, the user may practice with the equipment for a certain time period until he or she reaches a desired level of proficiency. The user may then check in with the provider of the application and perform CPR in a controlled testing situation to become certified in CPR, a certain aspect of CPR, or in another care giving technique for which the provider is authorized to provide certification. Also, the user may obtain the application from a first organization and may obtain certification from another organization. The provider of the application may also notify the user when they have reach an adequate level of proficiency that they may be able to obtain certification, and can remind a user when he or she needs to renew a certification. Moreover, the user's device or a related device may capture information in addition to motion information during the testing, such as by capturing audio or video that may be analyzed manually or automatically to further determine whether the user has adequately performed so as to be certified. Moreover, real-time connections may be made between the trainee and a certification tester so that real-time direction and feedback may be given, such as using a dual camera smartphone like the HTC EVO 4G.

In one implementation, a computer-implemented method for managing rescue training is disclosed. The method includes registering a plurality of individuals as potential rescue trainees through a central computer server system, receiving from computing devices that are remote from the central server system information indicative of rate and depth of compression for ones of the potential rescue trainees, generating comparative data that reflects performance of CPR chest compressions for a first rescue trainee against other rescue trainees, and providing the comparative data over a network for review by one or more of the rescue trainees. The method can also include distributing to the plurality of potential rescue trainees a training application that translates measurements from a hand-held device containing an accelerometer into information about chest compression depth and rate for a trainee. Moreover, the method can include organizing a campaign comprised of a plurality of lifesaving events to be performed by rescue trainees, and the plurality of lifesaving events can include two or more events selected from the group consisting of CPR with feedback, CPR without feedback, CPR performed on an avatar in a videogame, and CPR performed with visual feedback with an animated character in a videogame. In addition, the method can comprise organizing the plurality of rescue trainees into a plurality of groups that each include a plurality of rescue trainees, and tracking performance of the rescue trainees according to the group to which they belong. Moreover, the method may include identifying a plurality of exercises and assigning one of the plurality of exercises to a member of each of the groups, or the method may include generating one or more reports that indicate performance of a first group relative to one or more other groups.

In certain aspects, the method further comprises automatically accessing a contacts or social network list for a rescue trainee and providing invitations to members of the contacts list to be rescue trainees. In one implementation, the social network contacts of the rescue trainee or an avatar of the social network contacts become a reactive feedback indicator of the success of the rescue trainee's efforts to perform adequate compression depth. The rescue trainee could have the option to perform rescue skills on any number of individuals or likenesses. The social network members can function individually or as a group in performing rescue skills in the practice gaming environment. The information indicative of rate and depth of compression for ones of the potential rescue trainees can also be generated by an accelerometer on a computing device. Moreover, the method can include generating an indicator reflecting a level of fatigue in a rescue trainee using information indicative of rate and depth of compression over a time period, and ranking the rescue trainee using the generated indicator reflecting the level of fatigue.

In another implementation, a computer-implemented system for managing life-saving training comprises a game server programmed to coordinate results received from a plurality of gaming devices that include accelerometers for determining depth and rate of compression for performance of CPR. The game server includes a user registry that correlates registered users with computing devices that report performance metrics for users performing life-saving operations, an interface programmed to provide to the computing devices instructions regarding exercises to be completed by the users, and to receive from the computing devices information regarding proficiency with which the exercises were completed, and a comparison module programmed to compare one user's performance of one or more exercises against one or more other user's performance of the one or more exercises. The game server system may also include an electronic campaign manager programmed to combine a plurality of exercises into a campaign of exercises, for trainees to be assigned to each of the exercises in a campaign.

In other aspects, the electronic campaign manager is further programmed to organize individual trainees into groups and the comparison module is programmed to compare users according to groups into which they are organized. The exercises can include two or more events selected from the group consisting of CPR with feedback, CPR without feedback, CPR performed on an avatar in a videogame, and CPR performed with visual feedback with an animated character in a videogame or other likeness including the image of the rescue trainee or members of his social network The system can also include a social networking module programmed to identify contacts of registered users and to notify the identified contacts about availability of training using the game server.

In certain aspects, the game server is programmed to response to a plurality of identical training applications that translate measurements from a hand-held device containing an accelerometer into information about chest compression depth and rate for a trainee. The system can also include a report generator to produce one or more electronic reports that indicate performance of a first group relative to one or more other groups.

In another implementation, a computer-implemented system for managing life-saving training is disclosed that comprises a game server programmed to coordinate testing results received from a plurality of gaming devices that include accelerometers for determining depth and rate of compression for performance of CPR. The game server includes a user registry that correlates registered users with computing devices that report performance metrics for users performing life-saving operations, an interface programmed to provide to the computing devices instructions regarding exercises to be completed by the users, and to receive from the computing devices information regarding proficiency with which the exercises were completed, and means for producing comparative test results reflecting one user's performance of one or more exercises against one or more other user's performance of the one or more exercises.

The details of one or more embodiments are set forth in the accompanying drawings and the description below. Other features and advantages will be apparent from the description and drawings, and from the claims.

DESCRIPTION OF DRAWINGS

Like reference symbols in the various drawings indicate like elements.

DETAILED DESCRIPTION

This detailed description discusses examples of implementations that may be employed in executing and managing competitions among different people (registered users) who want to learn lifesaving techniques through an automated training process, and in locations that are convenient to them. Generally, different users may be allowed to download one or more applications that may use the accelerometers in their mobile computing devices to detect distance and rate of repeated motions, in an effort to judge the users' depth and rate of chest compressions in simulated settings. For example, the registered users may practice chest compressions and other lifesaving techniques on a dummy or foam block.

A server system may identify tasks for the various registered users and may receive information regarding how well each user performs his or her tasks. The server system may then compare the work of each registered user, such as to rate the users in a competition. The server system may also provide each user with information that indicates how that user is doing in a competition. Users may also be organized by the system, or may organize themselves, into teams that can compete against each other (e.g., where the teams may be formed around a school, workplace, particular groups of healthcare professionals such as competing fire stations or EMT crews, and the like). Thus, for example, different advertising agencies in a particular town may form teams and compete against each other in a contest that is sponsored by a local healthcare organization. The competitions may include various CPR simulations for which the actions of team members are measured, and results are compiled by the server system. The particular simulations may be made realistic, such as by notifying team members about a nearby sudden cardiac arrest, placing a CPR dummy in their place of business, and then measuring their response time and their proficiency at administering CPR.

Figure 1:
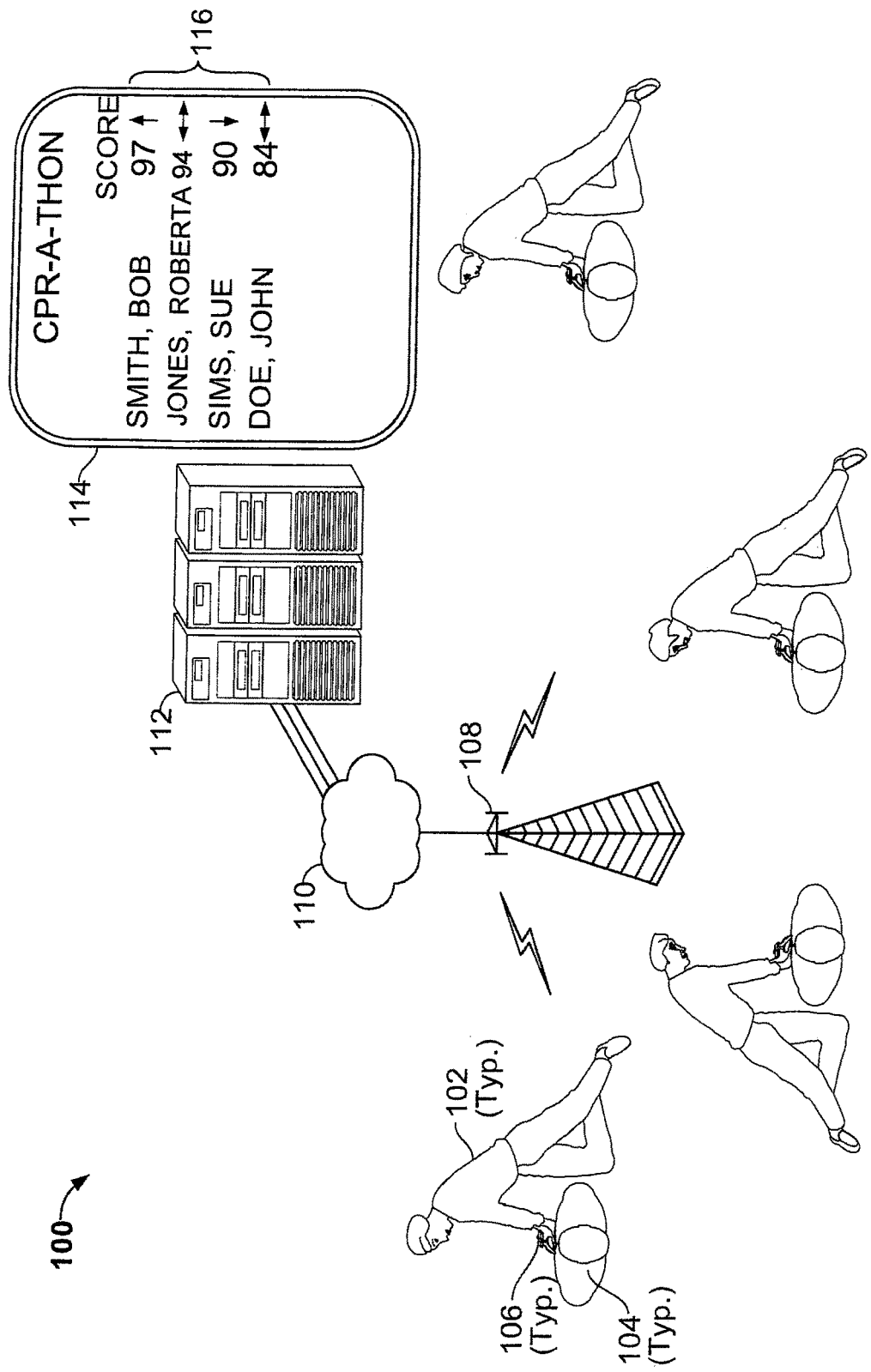
FIG. 1 is a conceptual diagram showing a group of users practicing CPR in communication with a central tracking system.

FIG. 1 is a conceptual diagram showing a group of users practicing CPR in communication with a central tracking system. In general, a plurality of users are shown performing CPR on dummies, where each user has strapped to his or her hand, an electronic device that includes an accelerometer for determining how well the user is performing chest compressions on the dummy, as part of a CPR training exercise. The relative performance of each user is collected by a central system, and the comparative performances of the various users can be provided back to the users by the system so that the users know where they stand vis-à-vis other users.

In particular, a system 100 is shown in which a typical user 102 performs chest compressions as part of CPR on a typical dummy 104 using a portable device 106 that has inside of it an accelerometer. By placing the accelerometer under or on top of the user's 102 hands and double integrating, the device can measure the vertical displacement of the user's hands, and in turn of the dummy's chest. American Heart Association guidelines dictate proper chest compressions according to depth of compression and rate of repetition, and therefore the device 106 can provide an appropriate measure by which to measure whether the user 102 is performing the chest compressions properly. Direct feedback may be provided to the user 102 by the device 106, such as by a visual (on the device screen, when the device is, e.g., a smart phone) or audible (via a speaker on a speakerphone) indications. For example, the device can display or state "push harder" or "push softer," or "push faster" or "push slower." The device may also beep with a metronome so as to guide the user 102 in the proper speed. Each user 102 may also choose to have unguided chest compressions so that they can test their ability to perform proper CPR without help—in case they find themselves in a situation in which their device 104 is not available.

In certain instances, the devices 106 may communicate through a wireless network 108, such as a cellular telephone data network and over a wired network 110, such as a network that includes the internet, with a central server system 112. The central server system 112 is shown in this example as a number of computer racks, to indicate that such a system may be part of a large server system, such as the MICROSOFT XBOX LIVE service. Alternatively, the devices 106 may communicate directly with each other or with a local server, such as by using a local WiFi or BLUETOOTH network. Each of the devices may be at the same level in such an organization, or one of the devices 106 may be elected as a controlled, and may receive information from other devices and then compile and distribute the information to the other devices 106.

The server system 112 is shown in the example as compiling certain information about the users 102 of the devices 106. In particular, applications that are installed on the devices may report information to the server system 112, such as via HTTP request or other appropriate mechanism, where the information indicates what chest compression and other CPR exercises have been performed with the device, and how well the user 102 performed each particular exercise. Such performance data may include data that reflects how deep the chest compressions performed by the user were, and at what rate they were performed. Both the average rate and depth, and the average variability in rate and depth may be reported. More detailed information can also be provided for further analysis by the server system 112, such as data indicating the time and depth of every chest compression during an exercise.

The server system 112 is shown in the figure as having generated a report 114 relating to the performance of each of the users 102. This report 112 is in the familiar form of a ranked listing of scores 116 for each user, with the highest scoring user (Bob Smith) at the top, and the lowest scoring user (John Doe) at the bottom. Arrows are also shown to indicate the trend in the scoring, since the competition is still occurring, with Sue Sims, for example, trending downward and in peril of falling below John Doe. The report 114 may be provided in code for display in the form that is shown on each of the devices 106 or on a central monitor if all of the users 102 are in a common location. For example, the users' devices 106 could display information relating to their performance (e.g., feedback on the performance of their chest compressions) and a computer monitor that is visible to the users if they look up can display the report 114. In this manner, each user can, during a timed exercise, focus on his or her own performance but can also look up to see how he or she is doing relative to other competitors.

Users can also be measured in terms of fatigue. In particular, certain users may perform chest compressions very well, but only for a short period of time. Such users are not helpful to a victim who needs extended chest compressions while waiting for professional responders such as EMTs. Thus, the systems discussed here may track trends in a user's performance, such as the degree to which the user varies from a standard norm (for depth and rate) over time so as to develop a measure of fatigue for the user. Such a measure may be provided separately in ranking a user, or may be combined with other factors in determining a user's score.

The measure of fatigue could also be used to provide real time feedback for a user. For example, an avatar pictured on a user's device may be made to sweat, pant, or turn blue, if readings from the device indicate that the user is starting to become fatigued. Such displays may cause a user to redouble his or her efforts to achieve a proper depth of chest compressions at a proper rate.

In addition to simply having the users 102 perform CPR, the system 112 may also provide to each user 102 different types of challenges or exercises that involve CPR-like motions but can provide a sense of variety for a user. For example, the users' 102 devices 106 may be made to display balloons and the users may inflate the balloons to a level that keep them aloft by compressing their dummies at an appropriate rate and depth. The feedback to a user may also be in the form of an avatar who smiles when depth of motion and rhythm of the motion are appropriate for chest compressions. Thus, actual numbers for either factor need not be displayed to a trainee, and such an approach may provide the trainee with an even more intuitive sense of the level of force needed and the appropriate rate. Other games may also be provided that focus on depth and rhythm, and a user may be cycled through the different games so as to maintain the user's attention and maximize the amount of training the user wants to do. The success may be indicated by reanimation of an avatar caused by sustained proper rate and depth of chest compression. Licensed characters or celebrity images could be used to provide the users entertainment options, as could the users own likeness.

The users 102 may also be provided with challenges that do not involve performing chest compressions, but that also affect the users' 102 standing in a competition. For example, users 102 may be given multiple-choice, true/false, or other forms of quizzes to test the users' 102 understanding of necessary lifesaving techniques. The users 102 may also be asked to perform other exercises that involve demonstrating their skills and/or knowledge for lifesaving.

The scope of training may be passed to other users as a mechanism to interest others in being trained in CPR. For example, a user who registers with a system like that described here may make his or her contacts, such as contacts stored at a social networking site like FACEBOOK, available to the system. The system may then send invitations to the friends to see if they would be interested in training. As an example, a first user may choose to train on an avatar that contains a second user's face, and after the training, the second user may be sent a message that says: "Bob just saved your life. Click here to see how you could save someone else's life." Separately, a message could be posted to the first user's page indicating that they have saved someone, thereby potentially interesting others of the user's friends (and their clicking on a link that accompanies the message could begin an automatic download process of the application to their relevant portable communication device). For example, just as users can now program a scale to report their weight on TWITTER every time they step on the scale, they could program their smartphone to report their progress each time they conduct a CPR training exercise. Users could also select "victims" conveniently, such as by having a training application automatically gather names in a contact list for the user, and presenting the names to the user as potential victims. The system could also present a list of famous people to be saved. Also, results of CPR and other competitions may be posted to areas in which other users can see them, so as to stoke the interest of those other users in training and competing themselves.

In certain situations, the competitions may be ad hoc. For example, a first user may send a message to one or more other users challenging them to an immediate CPR exercise, which may force them to drop whatever they are doing, and may thus better test their ability to react under pressure and also train them to react better under pressure. Also, such ad hoc triggering may be automatically generated by a system as part of a tournament or other competition.

The various exercises may also take into account a number of factors that define a good rescuer. The performance of chest compression may be one such factor. However, a user's knowledge of rescue techniques may also be important, and the user may be provided standard tests (e.g., multiple choice or fill-in-the-blank). Also, periodic short tests may be sent to a user, such as by sending that a "ping" notifier that a test is ready, having them confirm that they want to see the test, and then taking their answer (and perhaps timing how long it took them to provide the answer). Such tests may involve providing the user with a description of a hypothetical emergency scenario, and obtaining an answer of what the user would do in that scenario.

The training may also be integrated into existing training and recognition systems in additional ways. For example, an organization such as the Red Cross may use such techniques to modify its training and certification processes, and the difference in the type of training provided here (which can occur more frequently than typically annual CPR classes) may change the type of things that such an organization tests for. Also, users of such a system may acquire points with their employer, an insurer or HMO, or an organization such as the AHA or Red Cross, in order to motivate the users to improve their proficiency at CPR. The points may be used to purchase virtual items, such as for an avatar in a CPR game—also, a user's avatar may interact with other avatars, and may receive clothing or other visible indicators that show other users the status if the first user with respect to CPR or similar capabilities. For example, a user who has passed a life-saving course may have a red cross placed on his or her clothing in a service such as SECOND LIFE.

Such systems may also be used to expand the user's interests and training into additional public health areas. For example, users who demonstrate an interest and proficiency with the aspects discussed here may be provided with information about EMT training courses (where the courses may help underwrite the costs of such a system).

Figure 2A:
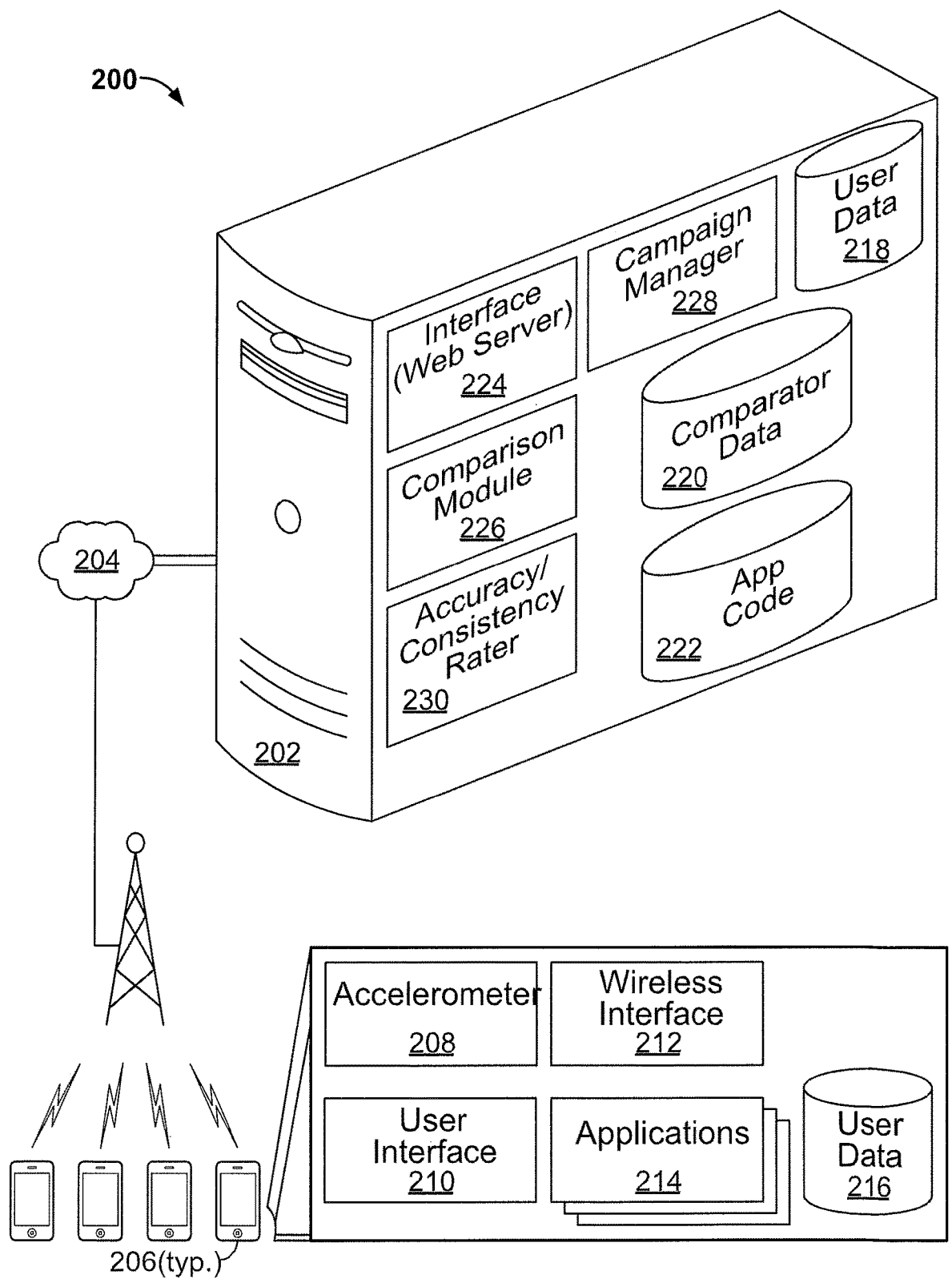
FIG. 2A is a block diagram of a system for managing CPR competitions among a plurality of registered users.

FIG. 2A is a block diagram of a system for managing CPR competitions among a plurality of registered users. In general, the block diagram shows more detail regarding the way in which a server system 202 may organize and manage a CPR or similar competition between users of mobile devices 206. Though shown as touchscreen smart phones in this example, the devices could also take the form of controllers for console gaming systems (e.g., WII MOTES).

In this example, the typical mobile device 206 can take a familiar form, such as a pre-existing smart phone that is augmented by application-specific programs. For example, the device 206 may include an accelerometer 208 whose readings are accessible through a published and standard application programming interface (API) to various software applications running on the device 206. The device may also include a user interface, which may be responsible for generating output to a user, such as by managing the organization and presentation of applications on a display of the device, and receiving input from a user, such as input in the form of motion of the device (via the accelerometer 208) and contact with a physical or touchscreen keyboard and display. A wireless interface 212 may also be provided on the device 206 so that the device 206 may communicate voice and data to a remote service, such as service provided by server 202.

The device 206 may also store a number of applications 214, some of which may have been provided with the device 206 and some of which may have been loaded later by a user of the device 206. The applications 214 may include personal productivity applications, educational applications, games, and other such applications. Certain of the applications 214 can capture sensed data form the accelerometer 208 and analyze the data in the context of assuming that the data represents chest compressions performed by a user of the device 206, or can provide such data for analysis by the server system 202.

The server system 202 may itself include a number of components needed to analyze and organize lifesaving actions by users of the devices 206. For example, the server system, 202 may include an interface 224, which may take the form of a web server or other appropriate interface for communicating with a plurality of client computing devices over a network, that may process data received from the devices 206 and provide the data to the appropriate component of the system 202. Certain of the data may be identified by a sending device 206 as having been generated from an accelerometer of a device 206 while a CPR application was running on the device. Such data may be provided to an accuracy/consistency rater 230 which may apply the data against known standards for the provision of chest compressions as part of CPR.

Such data for multiple different devices 206 and corresponding users may then be provided to a comparison module 226. The comparison module 226 can be programmed to compare various types of data from various users in a variety of manners. For example, the comparison module 226 may generate composite scores for the performance of each user, and can provide such scores in a report form for review by the users, so that each user can see where they stand relative to other users. Additional data, such as results of users who have taken quizzes on lifesaving techniques, may also be provided as separate scores and/or can be rolled into a composite score for each user.

Users may perform multiple exercises, or multiple users may be joined into cooperative groups using a campaign manager 228. The campaign manager may operate to determine what groups to be set up, may enroll users according to the groups, may issue challenges to users within each group, and may track progress of teams or groups in response to the challenges. The campaign manager, for example, may be responsible for checking a user's contacts (e.g., on a local device or in a social networking site) and providing notices to such contacts to establish users who may want to be involved.

The campaign manager may, for example, establish a lifesaving tournament within and among schools. Students within a school may compete against each other in CPR using accelerometer-equipped (or force-sensor equipped) devices, and may move forward in a traditional tournament style as they defeat other students. The losing students may be encouraged by the system to continue practicing, such as where a tournament is double elimination. A winner for each school may then be identified and may move on to compete against winners from other schools. Such a tournament could be "virtual," in that the geographical location of students would not matter, as long as a supervisor was available to ensure that the contestants performed honestly.

As another example, a variety of companies may cooperate, through a non-profit heart-healthy organization, in a fundraising and awareness raising campaign. Part of the campaign may be directed at teaching members (e.g., employees) or the organizations to perform lifesaving techniques such as CPR. The server system 202 may then assign challenges to individual users in a coordinated manner, for example, by assigning each one user from each organization to perform a particular task from a candidate group of tasks. The campaign manager, in association with the comparison module 226, may then roll up all of the actions of the various users so as to report performance to standard by group. Members of the groups may then review the results during the campaign in order to determine how they are doing. Such actions may then prompt members of the groups to do more, and to practice their CPR techniques more, in order to gain bragging rights over other organizations and the like.

Various data stores may be managed by the server system 202 in furtherance of the objective just stated. For example, a user data store 218 may store test data, identification data, and other relevant data for particular users who are registered with the system. A comparison data store 220 may store reports or other information that shows the performance of one user or group of users to the performance of other users or groups of users. An application code data store 222 may store code that users may download to their devices 206 to have the devices 206 test them in the various manners discussed in this specification. Such application code may be provided directly to users via the server system 222 or indirectly, such as via an internet-accessible app store.

The system 200 may also be established to permit progressive operation for a user. In particular, as a user's skills increase, the user can be matched against progressively better competition, so that a "campaign" may be considered to be a manager series of head-to-head competitions with other competitors who currently have comparable skill levels, and a user may try to move his or her way up through the rankings while constantly keeping an eye on his or her progress.

Figure 2B:
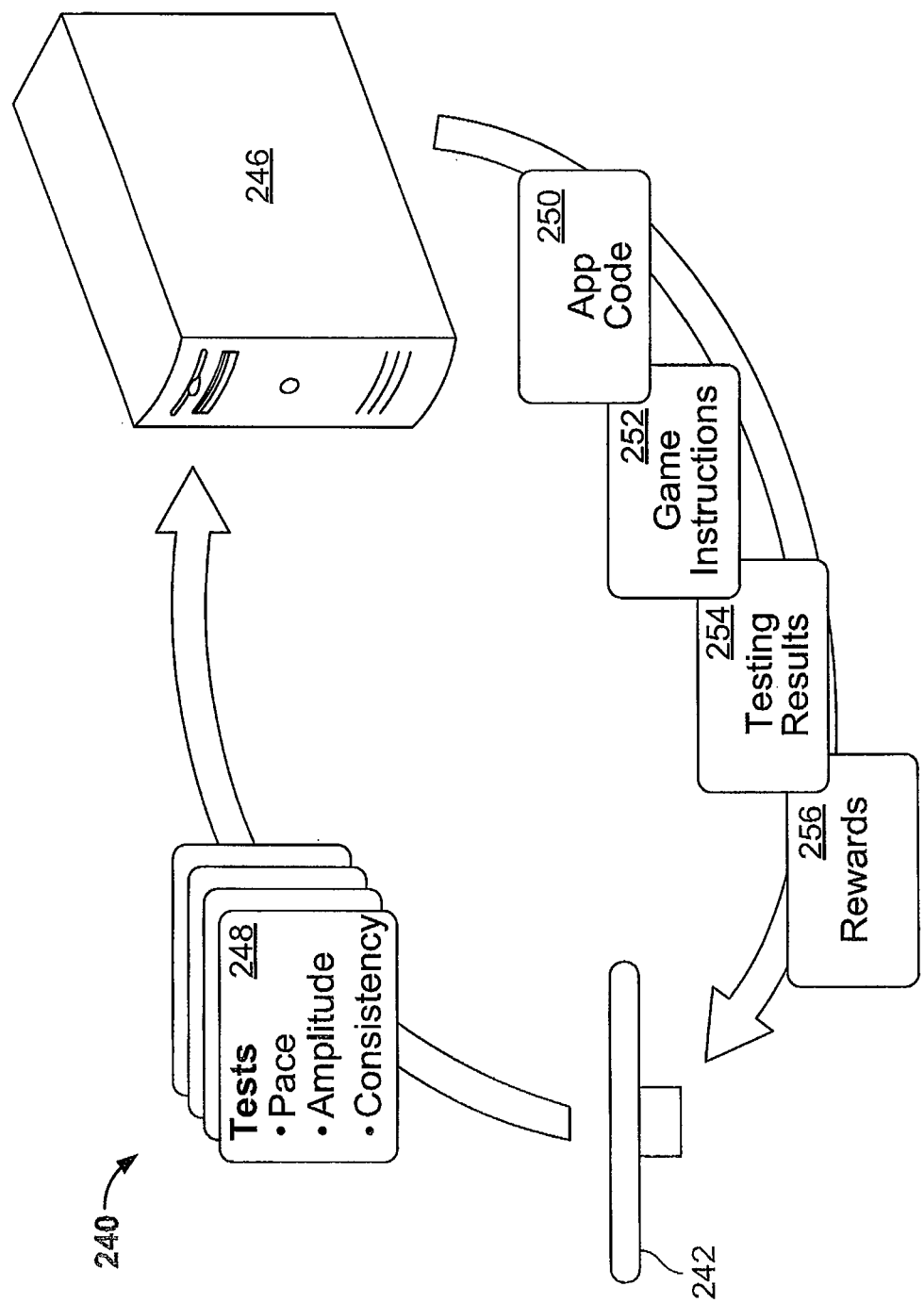
FIG. 2B is a schematic diagram showing example information flow between a server and a mobile device used in CPR training.

FIG. 2B is a schematic diagram showing example information flow between a server 246 and a mobile device 242 used in CPR training. In general, the figure shows examples of the sorts of data that the mobile device 242 may pass to the server 246 that is organizing a competition for lifesaving, and the types of information that the server 246 may pass back to the mobile device 242. In this example, the mobile device 242 takes the form of a smart phone or app phone that includes an accelerometer and/or other sensors needed to measure a user's proficiency with lifesaving techniques such as CPR.

In the example, the mobile device 242 may send the server 246 data form sensors regard the performance of various exercises by a user of the device 242. Such information may include data representing, of from which can be calculated, the depth of individual or grouped chest compressions performed using the device 242. For example, raw accelerometer data may be passed, or a list of numbers may be passed that represent particular depths (e.g., measured in centimeters or inches) that can be used by the server 246. Another list may represent the time at which each compression began or ended. Such data may also be sent in a table or other appropriate data structure. Other data that is sent by the device 242 to the server 246 may include responses by a user to test questions provided by the server 246 and posed to the user by the device 242.

An arrow moving from the server 246 to the device 242 shows examples of data that can be sent downward from server to client. For example, application code 250 may be provided, either from the server that manages a training process or from another server such as a public app server operated by a hardware or OS manufacturer or group (e.g., the ANDROID group). The application code may generate a variety of applications, from simple lifesaving testing applications (which may be hosted applications delivered via web page) to basic CPR applications, to full-blown immersive games that include a chest compression component as one of many portions of a larger entertaining game.

Game instruction may also be provided (box 252). For example, instructions on how to perform chest compression may be provided, along with instruction on how to operate an application so that a user's data may be uploaded to the server 246. Also, testing results 254 may be downloaded to the device 242. While the device 242 may be capable of displaying results for testing that occurred on the device 242 itself, the additional results 254 may show results from the testing of other users and also comparative results that show how one user performed in comparison to other users.

Finally, rewards 256 may be downloaded from the server 246 to the client 242. For example, where a group of organizations organizes a series of exercises in the form of a campaign for which members of the organizations can compete with each other, rewards can take the form of recognition (e.g., one company can have bragging rights over another company). The rewards may also take the form of coupons or other certificates for users who have completed a campaign to obtain free food or other discounted merchandise or services.

Figure 3A:
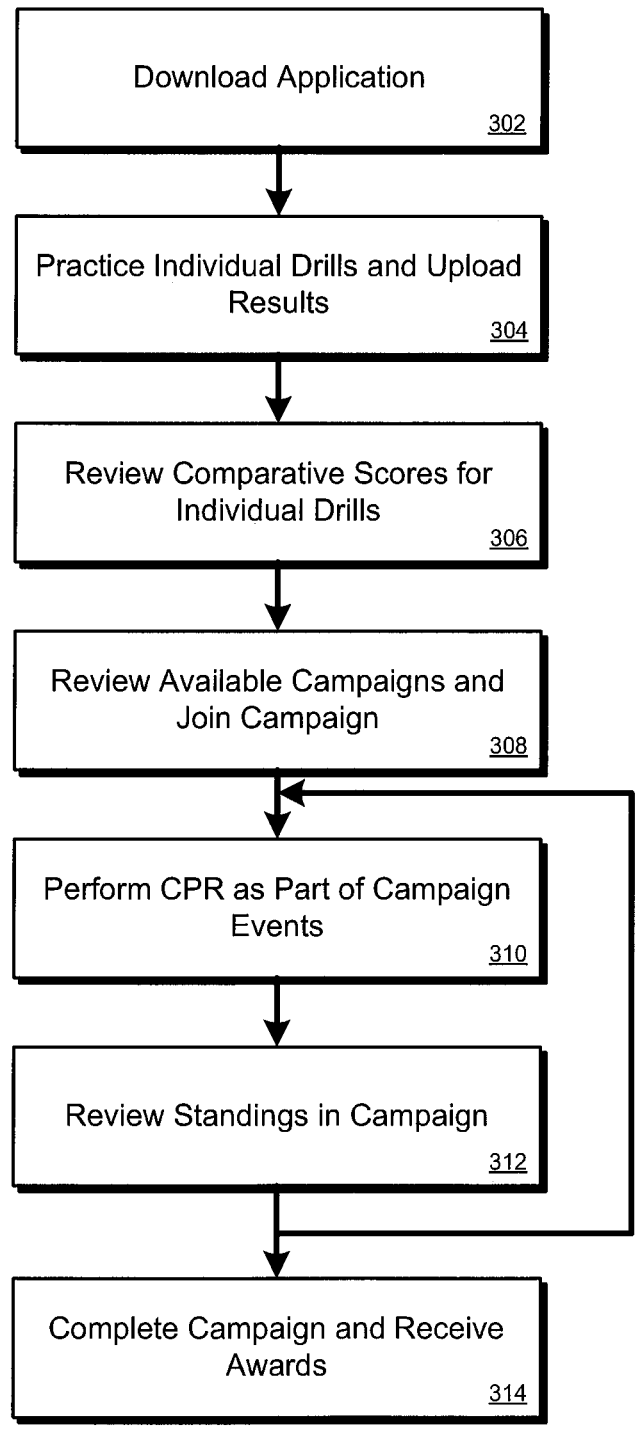
FIG. 3A is a flow chart of a process that a user may follow in participating in a CPR competition.

FIG. 3A is a flow chart of a process that a user may follow in participating in a CPR competition. In general, the process involves a user of a mobile computing device (e.g., a smart phone or app phone) downloading a CPR training application to the computing device and interacting with the application. After a time period, the user may choose to enter a competitive campaign that involves responding to prompts to use the CPR application in order to demonstrate proficiency with administering CPR. The process may track the user's proficiency, provide a user with a score for that proficiency, and compare the proficiency against the proficiencies of other users who are registered with the process.

The process begins at box 302, where a user downloads a CPR training application. Such a download may occur in a familiar manner, such as by the user visiting an app store on the Internet and selecting an application for download. The application may be provided for free or for a charge.

At box 304, the user practices individual CPR techniques. For example, the user may obtain a foam block that is intended to represent the compliance of a human chest during CPR, and may use their CPR application and mobile computing device on the block. As one example, a user may have previously owned a smart phone that includes an accelerometer and may have purchased a jacket for the phone equipped with a hand strap, such as the iSkin Pulse. The user may place the strap around her or her hand so that the screen of the smart phone can be seen by the user while performing chest compressions and the smart phone may move in tandem with the user's hands performing the chest compressions. The smart phone screen or a speaker may be used to provide guidance to the user in performing chest compressions. For example, the smart phone may show the user an appropriate pace and their actual pace on the screen, and may also state "push faster", "push slower", "push harder", or "push softer."

At this stage, the exercises may be relatively basic and may simply test a user's basic ability to perform chest compressions at an appropriate rate with appropriate depth of compression. After a certain period, the individual may ask to see their scores as compared to scores of other users, at box 306. The scores may take a variety of forms, and are generally based on the accuracy of the user with respect to depth of compression and pacing of the compressions, and the ability to not vary far from standard values for depth and pace. The scores may also be kept separately for assisted training and unassisted training, where assistant training involves the user's computing device giving them feedback with respect to pace and depth, and unassisted training involves no such feedback and is thus more difficult for a user. Thus, a user can readily see whether they should perhaps have additional practice with unassisted training (in case they are required to perform chest compressions on a real victim when their mobile device is not available to them).

If the user has enjoyed what they're doing so far, they may choose to join a training campaign at box 308. Such a campaign may involve a series of training exercises so as to better test the ability of the user to perform under varying conditions. For example, at certain points in a campaign, the user's device may simply make a noise to indicate that CPR needs to be performed, and the user will be required to start performing the CPR as quickly as possible. In such a manner, the training may better replicate the true situation of CPR the real world, where a rescuer does not have an opportunity to get ready to perform CPR. In addition, the response time for the user may be measured so that the user is required to react quickly, as they would be required to react in a real-world situation.

The CPR exercises can also be built into one or more video games so as to test the player's execution in a real-world setting. For example, one video game could involve a player taking on the role of a police officer, and in the game a police officer may come upon a person suffering from cardiac arrest. Thus, in addition to the various responses that the player would have to make in the game as a real police officer, the player can also be required to perform simulated CPR on the simulated victim. The game could be played on a home console, with the player's portable computing device used simply for CPR mechanism, or the game could be played on a portable device itself. Where the game is played on a home console or computer, the user may be registered with a networked gaming system so that the system can identify both the user's home console and the users portable device, and register inputs from both devices as being related to the user. The CPR device may also be a console controller that includes an accelerometer, such as a WIIMOTE.

The campaigns may also be related to groups of users in addition to individual users. In one example, professional organizations may compete against each other to improve their ability to provide life-saving response. For example, multiple different law firms may compete in a week-long competition to score points and thereby gain bragging rights over each other. (The competition may also be directed to raising charitable donations for various heart-health organizations.) Such a competition would have the salutary effects of increasing awareness of heart health and lifesaving techniques, and of improving the life-saving ability for each member of the various teams. Thus, for example, a user at box 308 may navigate through menus provided by a central server to identify their employer, or may enter the name of the employer as a search term, and may be presented with a campaign that has already been designed by central facilitators for their employer.

The user's name may already be listed for the campaign and they may enroll at box 308. Such enrollment may then place them to be ready for the campaign, which may involve a number of different exercises that are presented to registered users of the different organizations that are part of the campaign. For example, organizers of the campaign may visit each enrolled organization in turn, and trigger a "random" CPR notices for each of the people that is registered with that organization. The organizers may have put CPR dummies in, for example, a cafeteria at an employer's place of business, and may generate a message to the portable computing device of each registered user, requiring them to come to the cafeteria as quickly as possible to perform CPR on the dummies. Performance may be a combination of response time (perhaps normalized for each user's distance from the cafeteria) and CPR performance. The performance of each user may be measured in turn, and the team from that organization may be provided with a composite score based on the performance of each member. Such activities are shown at box 310.

As part of a group campaign, registered users may be required to perform a variety of other exercises. For example, a first exercise may be simple guided CPR, in which the users' devices provide them feedback as they perform the CPR. The second exercise may involve simple unguided CPR, where the users receive no feedback about the exercises, but the exercises are performed in a predictable, calm situation, and in a repeated fashion so that the users can focus on proper performance of the exercise. A next exercise may involve the playing of a role-playing game in a controlled environment, where the user comes upon a character in need of first aid attention, and then is required perform CPR on the character, and their performance is measured by the system and uploaded to a server for composite scoring in the campaign. A next set of exercises may be like those above, were a user is summoned without warning to perform CPR at a location that is remote from where they are currently located. Other sorts of exercises may also be encompassed by a campaign.

At box 312, users are permitted to review their standings within the campaign. In particular, after each exercise, data that represents a user's performance of an exercise may be uploaded to a central server that manages a campaign. In general, the data may represent the ability of the user to meet predetermined standards regarding a pace of providing chest compressions and compression depths of the chest compressions.

Users may also be asked to perform other operations, such as by answering quiz questions related to the proper delivery of CPR and other life-saving techniques. For example, a user may be shown a photo or a drawn picture of a hypothetical victim and may be asked to indicate how the victim is to be properly treated. The user may also be asked to make various diagnoses based on hypothetical facts, which can include pictures of victims or injuries on victims.

The standings for a campaign may be organized in a variety of manners. For example, when the campaign involves only individuals, each individual may be assigned a composite score that indicates how well they performed the various exercises, and the individuals may be ranked from top score to bottom score so that each individual can see where they currently stand in the standings, and what they need to do to maintain or improve their position.

For group campaigns, the groups may be ranked in various manners, and a user may be allowed to click on a particular group to expand that group and see the scores of each of the users within the group. Each group may also be given multiple different scores, such as scores relating to level of participation in the campaign, average accuracy of users in the campaign, quiz scores of users in the campaign, and variability in accuracy of users in the campaign so that the campaign tracks organizations in which all users are pretty good, versus organizations in which some users are very good and some users are not at all. Users may also be allowed to see head-to-head comparisons between two different organizations or two different users, to better isolate the strengths and weaknesses of each organization (e.g., "our CEO is doing better than your CEO").

At box 314, the campaign is completed and users receive their awards. The completion of a campaign may be triggered by the occurrence of a certain time, such as when a campaign is predetermined to last one week. In such a situation, if a user has not finished a particular exercise by the end of the campaign, the user's score may be adjusted accordingly, such as by docking points for not completing the exercise. The end of the campaign may also be triggered by a central server system recognizing that all users have completed the necessary exercises for the campaign, or that a sufficient number of users have completed the exercises and that the campaign has been running for appropriate period of time.

At the end of the campaign, a central server system may close the campaign for data entry, and may generate a number of statistics to represent performance of individuals or organizations in the campaign. Such representations may involve graphical charts and other easy to understand representations of performance in the campaign. For example, bar charts may be prepared to indicate relative performance by different organizations in the campaign, where each bar is broken up to represent the relative contribution of each team member to the team's score. Such data may be organized into a report, which may be reviewed by various users who are registered with the campaign. For example, the central server system may generated a document and send it by e-mail to each registered user, or may provide a hyperlink in the form of a URL and may send the hyperlink to each user, who may then to be served a webpage or other document that shows the report of performance in the campaign.

Thus, in this manner the process shown here may provide for automated and enjoyable techniques for training potential responders to perform CPR. The techniques may be flexible to address various needs of different users. In addition, the techniques may permit organizations to be trained in CPR and other life-saving techniques as part of a contest. In this way, the organizations may make the training more enjoyable than under ordinary circumstances, and may obtain better turn-out and participation so as to make their employees or other members more adept at performing CPR, and thereby improve the safety of others within the organizations.

Figure 3B:
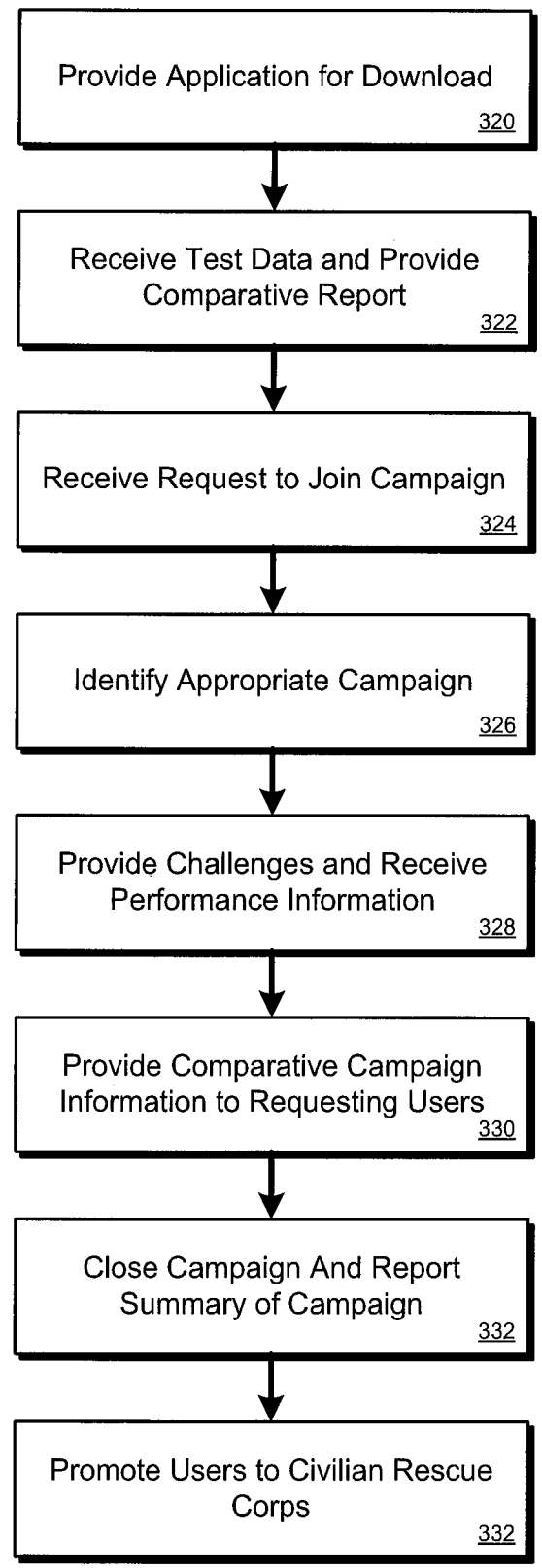
FIG. 3B is a flow chart of a process that a server system may employ in managing a CPR competition.

FIG. 3B is a flow chart of a process that a server system may employ in managing a CPR competition. In general, the process involves managing the enrollment of competitors in a lifesaving competition, in assigning exercises for the competitors to complete, and in tracking the performance of the various competitors relative to each other.

The process begins at box 320, where one or more applications are provided for download by potential competitors. The applications may be provided directly from a server that manages competitions, or may be initially uploaded to an app store that is available to the public in a familiar manner, and then downloaded from the app store by the various potential competitors. The application may be designed to run on one or more types of smart phones that have accelerometers built into them, where the accelerometers may be used to generate data for measuring compression depths and compression rate of the devices. Relative tilt of the devices may also be measured using the accelerometers, possibly in combination a magnetometer or compass on the device. Tilt of the device may be used to further refine measurements of how accurate CPR has been performed when using the device.

The applications provided to the devices may take a variety of forms. For example, an application may simply be a placeholder installation application that causes the downloading of additional material that is the actual application for measuring CPR itself. Thus, when a user invokes the first application, it may in turn install the actual application. Alternatively, the application may be a basic program for measuring CPR performed using a mobile device, and may also include training materials in the form of traditional written materials and quizzes regarding life-saving techniques (or may include code for accessing such materials over the internet). The applications may also include more complex games that place a player in a particular role, such as that of an army medic, police officer, emergency medical technician (EMT) or paramedic. Such gains may be relatively simple or complex, and may be larger games in which the life-saving techniques are only a small poor part of the game. Such larger games may be distributed through stores, and users may indicate when they install the games whether they have a device that includes an accelerometer, so that lifesaving opportunities may be enabled for such users in the games. (Certain consoles such as the WII may include standard controllers that contain accelerometers, and may thus be used by all players in such a role.)

At box 322, a central server system receives test data and provides comparative reports to registered users. Users may register as part of the download process for a game, and may provide identifying information for themselves so that the central system can better track them and their performance. In this step shown at box 322, a user may see how their performance compares against other users of similar experience, such as users who have recently downloaded the application or applications. Such a comparison may simply involve providing a score to each user and ranking the users according to their scores. The approach may also involve giving the user a letter grade in a familiar manner (e.g., A to F) and showing them that letter grade.

After a user has shown some level of proficiency in performing CPR and other life-saving techniques, such as by generating data on compressions that exceed a predetermined value and/or answering enough questions about life-saving techniques appropriately, the user may be allowed to move to a next level of the system, such as by joining a campaign to improve his or her CPR techniques. Thus, at box 324, the central system receives a request from the user to join a campaign. Such a request may be in made in response to a notification sent by the central system that indicates that the user may be allowed to join a campaign. The user may join a campaign generally by the system identifying for the user a campaign that the system selects based on the user's performance to date. Alternatively, the user may select a style of campaign that is offered by the system, such as an army medic or police officer campaign, if that is the type of role-playing that the user would like to be involved with. Alternatively, the user may identify a particular campaign by name or difficulty level.

Also, a user may join a campaign with a group such as a group of friends or co-workers. Such group campaigns may be directed toward improving the life-saving abilities of people who work together in a particular geographic area so as to make their workplace safer.

At box 326, the system identifies appropriate campaigns for a user, as just discussed. For example, if the user identifies himself as being an employee of a particular corporation, and that corporation has registered to establish itself as a participant in a competition, the user may be enrolled in the appropriate campaign for their employer.

At box 328, the system provides challenges and receives performance information from various users. At this stage, relevant users have registered with a campaign, and the campaign can begin. The campaign may involve a number of predetermined challenges or exercises that each user in the campaign is to complete. Various users may also perform different exercises than other users. For example, one employee in a group may be provided with a particular set of challenges along with corresponding employees from other groups. Other employees from each group may be provided with a different set of challenges (e.g., one team member can be required to do exercises A-D and another may perform C-F). However, in each instance, the teams are provided with a grouping of comparative challenges so that accurate observations and scoring may be made with respect to the various teams.

Each user may also be provided with challenges that depend on their performance in previous challenges. For example, challenges may be ranked according to difficulty, and a user may move up or down a series of challenges based on their performance in prior challenges or exercises. For example, if a user performs very well in one challenge, they may be skipped up more than one level in a layer of challenges so that they are always been pushed in their abilities.

Each campaign may involve a number of components in addition to the performance of chest compressions, as noted above and below. For example, enrolled participants may be asked to review training information on life-saving techniques be quizzed on the particular information. Quiz questions may also be integrated with particular life-saving scenarios. For example, a user may be sitting at work and be alerted by their mobile computing device. The alert may cause them to run to their corporate cafeteria and find a foam block for CPR a practice located there. Their device may then show them a drawing or picture of a simulated victim and asked them to make determinations about the victim, such as whether CPR would be appropriate or not. If CPR is appropriate, the user may then be asked to join their mobile device to their hand and began performing chest compressions on the foam block. The mobile device, through its accelerometer, may then measure the compressions and their depth and rate, and report all such information back to a central system, where the user may receive a composite score for the entire exercise.

At box 330, comparative campaign information is provided to requesting users. Such information may be provided throughout the course of the campaign so that different registered users may determine where they stand relative to other users or groups. The information may also be provided at the end of the campaign (box 332) to summarize the performance of various users or groups across the entire campaign. For example, at the end of the campaign, which end may be determined by the termination of a time period for a defined-length campaign or upon the completion by appropriate number of users of an appropriate number of exercises, the system may send out a link that users may select to see a web page that reports on the campaign. Such a report may show an individual or organization that scored the highest and thus won the campaign, and may also show various other sorts of information. For example, some organizations may not have the highest score may have had the highest participation and may be provided with awards for such participation. Other similar recognitions or awards may also be shown in the report.

Additional options may also be provided to users at the end of the campaign. For example, for users who have performed well in the campaign, the system may provide notice that they may advance to be part of a civilian life-saving corps for performing CPR and other life-saving techniques. Such a corps may consist of various registered users of mobile devices who are identified as having certain life-saving skills, and who have identified themselves as willing to be paged as necessary when a life-saving need occurs in their area. Thus, for example, when a dispatch service receives a report of a person having a cardiac arrest in an area, the dispatch service may cause a page or other notification to be sent to corps members in the area of the cardiac arrest event, and members who are interested in responding may respond appropriately. The dispatch system may then cause information about the event, including a map that shows a navigation line connecting the particular corps member to the location of the event. Such a dispatching system and related techniques are disclosed in U.S. Applications 61/261,276, filed on Nov. 13, 2009 and Ser. No. 12/946,803, filed on Nov. 15, 2010, now U.S. Pat. No. 9,232,040, which are herein incorporated by reference in their entirety.

Thus, by the techniques discussed here, a central server system may manage the training of CPR among a large number of registered users, and may increase the amount of training and diversity of training for each member by making the training into a competition by which users can compete with each other and compete in various games. Such a system may result in more people signing up for the training, in more complete initial training, in better follow-up by users to keep their skills sharp, and in group participation that increases the number of trained people even more.

Figure 3C:
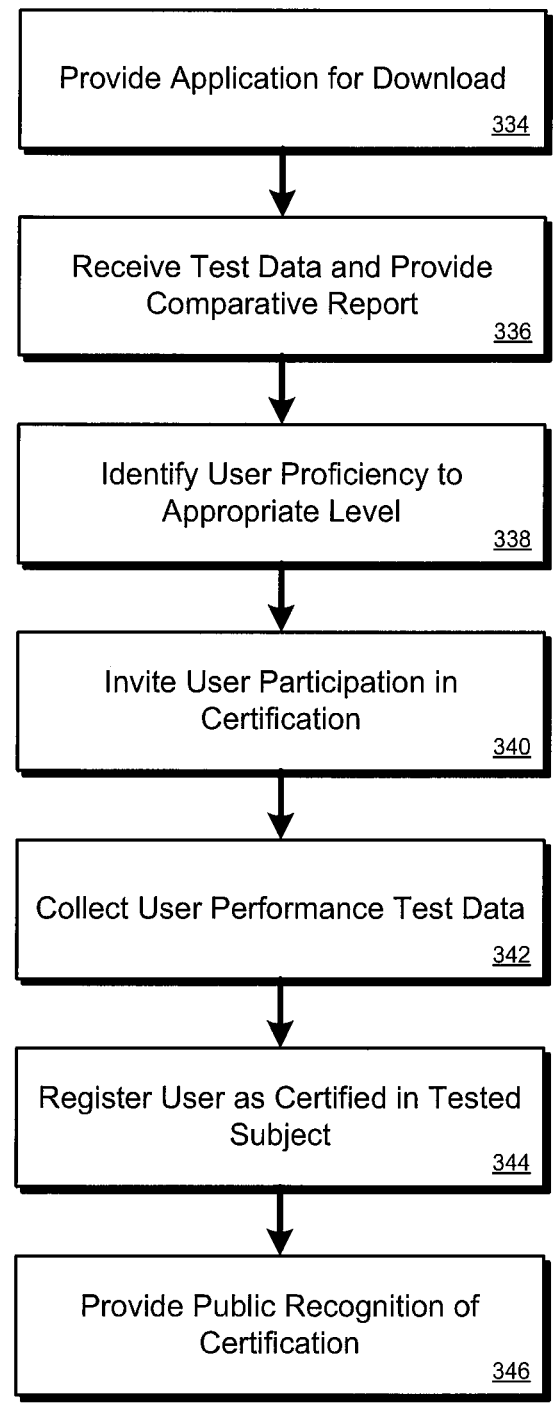
FIG. 3C is a flow chart of a process for remote life-saving certification of users of mobile devices that contain motion sensors.

FIG. 3C is a flow chart of a process for remote life-saving certification of users of mobile devices that contain motion sensors. In general, the process allows a user of a mobile computing device to be certified for life-saving techniques such as CPR in a flexible manner, generally on their own schedule.

The process begins at box 334, where a CPR training application is provided for download. The application may be the same as those discussed above and may be made available through a third-party public app store so as to make distribution of the application easy and convenient. The application may be provided free or for a cost, or may be provided free in a limited-capability trial version that is then followed by a paid full-featured version.

At box 336, a system receives test data from the user of the application and provides a comparative report to a user of the application. For example, the user may execute the application on his or her mobile smartphone and may practice CPR or other care giving techniques on a dummy, foam block, or appropriate testing subject. Information about the motion of the device and other information (e.g., a user's responses to questions posed on a screen of their mobile device) may be captured and uploaded to the system. The system may then analyze such information to determine a proficiency level for the user (box 338) on the way to determining whether the user is ready to be certified for a certain skill or standard such as Basic CPR. Such a determination may be made, for example, by determining that the chest compressions by a user match AHA guidelines in terms of rate and depth a certain minimum amount or proportion of time that the user is performing chest compressions with his or her mobile device. The determination may also require a user to perform other functions such as indicating that they are performing rescue breathing by pressing on icon on the screen of their device. At box 340, if the user shows proficiency, he or she is invited to test for certification.

Alternatively, a user may practice with the application and may receive feedback about their progress. They may then determine for themselves that they are ready for certification. Under either approach, the user's preparation may include competitions such as those discussed above, and a trigger for the user to test for certification may be the successful completion of a competition like those discussed above.

At box 342, user performance test data is collected. Such data may be collected under controlled test conditions, such as by having the user perform CPR on a standard foam training pad or training dummy while their device measures motion (e.g., acceleration and other motion data). The data may be similar to that collected during the training period, and would be sufficient to determine if the user performed satisfactorily under the applicable standards for certification. The data may include motion data from the user's mobile device, data concerning answers to quiz questions the user may have been posed during the testing exercise, and other data including audio and video data from the area around the test subject during the test.

At box 344, the user, if they meet the require proficiency standard, is certified in the relevant task or standard to which their testing was directed. Such certification may simply involve sending them a certificate (electronic or paper) and keeping a record that the person is certified for a certain time period. The certification may also involve making records that identify certified users available to certain requesters who may have an interest in identifying certified users in an area. As an extension, the certification status of a user may also be employed in asking the user to enroll in a rescue corps, and in locating contact information for the user so that the user, if they enroll with the corps, may be notified when an emergency situation occurs in their vicinity.

At box 345, a public recognition of the user's certification may also be published. Such publication may be as simple as adding the user's name and town to a list of certified users. The publication may also involve adding an item to the user's profile with a social networking web site. For example, such a site may display icons on a user's profile page that represent accomplishments by the user, in a manner similar to the display of badges with the FOUR-SQUARE web application.

In this manner, a user of a smartphone or similar device may easily download a CPR or similar training application and may become CPR proficient on their own schedule and in locations they prefer (as opposed to having to attend a formal CPR training course at a particular time and location). At an appropriate time, the user may be tested remotely with respect to his or her capabilities, and may be awarded a certification if he or she passes the testing. The certification of the user may then be extended to other implementations, such as recognizing the user in a social networking setting or presumptively adding the user to the rolls of other certified users who are selected to be contacted in particular situations.

Figure 4:
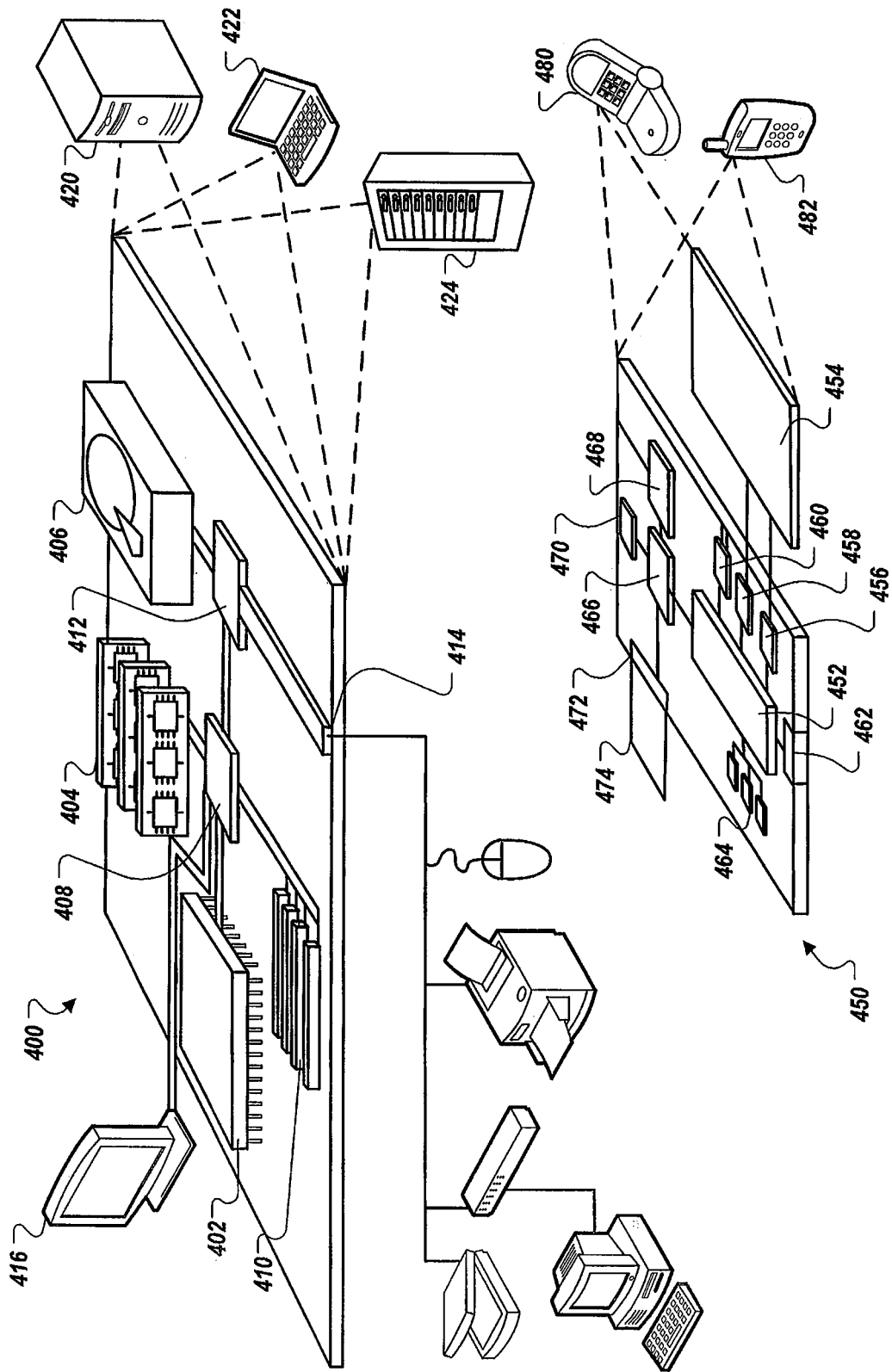
FIG. 4 shows an example of a generic computer device and a generic mobile computer device, which may be used with the techniques described here.

FIG. 4 shows an example of a generic computer device 400 and a generic mobile computer device 450, which may be used with the techniques described here. Computing device 400 is intended to represent various forms of digital computers, such as laptops, desktops, workstations, personal digital assistants, servers, blade servers, mainframes, and other appropriate computers. Computing device 450 is intended to represent various forms of mobile devices, such as personal digital assistants, cellular telephones, smartphones, and other similar computing devices. The components shown here, their connections and relationships, and their functions, are meant to be exemplary only, and are not meant to limit implementations of the inventions described and/or claimed in this document.

Computing device 400 includes a processor 402, memory 404, a storage device 506, a high-speed interface 408 connecting to memory 404 and high-speed expansion ports 410, and a low speed interface 412 connecting to low speed bus 414 and storage device 406. Each of the components 402, 404, 406, 408, 410, and 412, are interconnected using various busses, and may be mounted on a common motherboard or in other manners as appropriate. The processor 402 can process instructions for execution within the computing device 400, including instructions stored in the memory 404 or on the storage device 406 to display graphical information for a GUI on an external input/output device, such as display 416 coupled to high speed interface 408. In other implementations, multiple processors and/or multiple buses may be used, as appropriate, along with multiple memories and types of memory. Also, multiple computing devices 400 may be connected, with each device providing portions of the necessary operations (e.g., as a server bank, a group of blade servers, or a multi-processor system).

The memory 404 stores information within the computing device 4500. In one implementation, the memory 404 is a volatile memory unit or units. In another implementation, the memory 404 is a non-volatile memory unit or units. The memory 404 may also be another form of computer-readable medium, such as a magnetic or optical disk.

The storage device 406 is capable of providing mass storage for the computing device 400. In one implementation, the storage device 406 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 404, the storage device 406, memory on processor 402, or a propagated signal.

The high speed controller 408 manages bandwidth-intensive operations for the computing device 400, while the low speed controller 412 manages lower bandwidth-intensive operations. Such allocation of functions is exemplary only. In one implementation, the high-speed controller 408 is coupled to memory 4504, display 416 (e.g., through a graphics processor or accelerator), and to high-speed expansion ports 410, which may accept various expansion cards (not shown). In the implementation, low-speed controller 412 is coupled to storage device 406 and low-speed expansion port 414. The low-speed speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 400 may be implemented in a number of different forms, as shown in the figure. For example, it may be implemented as a standard server 420, or multiple times in a group of such servers. It may also be implemented as part of a rack server system 424. In addition, it may be implemented in a personal computer such as a laptop computer 422. Alternatively, components from computing device 400 may be combined with other components in a mobile device (not shown), such as device 450. Each of such devices may contain one or more of computing device 400, 450, and an entire system may be made up of multiple computing devices 400, 450 communicating with each other.

Computing device 450 includes a processor 452, memory 464, an input/output device such as a display 454, a communication interface 466, and a transceiver 468, among other components. The device 450 may also be provided with a storage device, such as a micro drive or other device, to provide additional storage. Each of the components 450, 452, 464, 454, 466, and 468, are interconnected using various buses, and several of the components may be mounted on a common motherboard or in other manners as appropriate.

The processor 452 can execute instructions within the computing device 450, including instructions stored in the memory 464. The processor may be implemented as a chipset of chips that include separate and multiple analog and digital processors. The processor may provide, for example, for coordination of the other components of the device 450, such as control of user interfaces, applications run by device 450, and wireless communication by device 450.

Processor 452 may communicate with a user through control interface 458 and display interface 456 coupled to a display 454. The display 454 may be, for example, a TFT LCD (Thin-Film-Transistor Liquid Crystal Display) or an OLED (Organic Light Emitting Diode) display, or other appropriate display technology. The display interface 456 may comprise appropriate circuitry for driving the display 454 to present graphical and other information to a user. The control interface 458 may receive commands from a user and convert them for submission to the processor 452. In addition, an external interface 462 may be provide in communication with processor 452, so as to enable near area communication of device 450 with other devices. External interface 462 may provide, for example, for wired communication in some implementations, or for wireless communication in other implementations, and multiple interfaces may also be used.

The memory 464 stores information within the computing device 450. The memory 464 can be implemented as one or more of a computer-readable medium or media, a volatile memory unit or units, or a non-volatile memory unit or units. Expansion memory 474 may also be provided and connected to device 450 through expansion interface 472, which may include, for example, a SIMM (Single In Line Memory Module) card interface. Such expansion memory 474 may provide extra storage space for device 450, or may also store applications or other information for device 450. Specifically, expansion memory 474 may include instructions to carry out or supplement the processes described above, and may include secure information also. Thus, for example, expansion memory 474 may be provide as a security module for device 450, and may be programmed with instructions that permit secure use of device 450. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 464, expansion memory 474, memory on processor 452, or a propagated signal that may be received, for example, over transceiver 468 or external interface 462.

Device 450 may communicate wirelessly through communication interface 466, which may include digital signal processing circuitry where necessary. Communication interface 466 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 468. In addition, short-range communication may occur, such as using a Bluetooth, WiFi, or other such transceiver (not shown). In addition, GPS (Global Positioning System) receiver module 470 may provide additional navigation- and location-related wireless data to device 450, which may be used as appropriate by applications running on device 450.

Device 450 may also communicate audibly using audio codec 460, which may receive spoken information from a user and convert it to usable digital information. Audio codec 460 may likewise generate audible sound for a user, such as through a speaker, e.g., in a handset of device 450. Such sound may include sound from voice telephone calls, may include recorded sound (e.g., voice messages, music files, etc.) and may also include sound generated by applications operating on device 450.

The computing device 450 may be implemented in a number of different forms, as shown in the figure. For example, it may be implemented as a cellular telephone 480. It may also be implemented as part of a smartphone 482, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

A number of embodiments have been described. Nevertheless, it will be understood that various modifications may be made without departing from the spirit and scope of the invention. For example, much of this document has been described with respect to ICU monitoring with attending physicians, but other forms of patient monitoring and reporting may also be addressed.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

What is claimed is:

1. A system for improving performance of chest compressions, the system comprising:
  a plurality of mobile computing devices, each respective mobile computing device of the plurality of mobile computing devices comprising:
    a housing configured to be held by a respective user when the respective user is performing chest compressions;
    a communication interface having a transceiver provided inside of the housing;
    an accelerometer provided inside the housing and configured to measure a vertical displacement of the hands of the respective user to determine information relating to rate and depth of chest compressions;
    a magnetometer provided inside the housing and configured to measure tilt of the respective mobile computing device,
    wherein raw accelerometer data from the accelerometer is received via an application programming interface (API) and double integrated and combined with tilt data from the magnetometer to measure the vertical displacement of each respective mobile computing device, and
    wherein determining the information relating to rate and depth of chest compressions comprises:
      generating depth data associated with depths of chest compressions and rate data associated with rate of chest compressions based on the vertical displacement measured by double integrating the raw accelerometer data and the tilt data from the magnetometer; and
populating a data structure based on the depth data and the rate data; and
a processor provided inside the housing and configured to control operations of the respective mobile computing device; and
a remote server system provided in direct communication with the plurality of mobile computing devices and configured to send information to and receive information from the plurality of mobile computing devices,
wherein the system is configured to:
associate, by the processor of each respective mobile computing device, the information relating to the rate and depth of the chest compressions with the respective user of the respective mobile computing device;
send, by the communication interface of each respective mobile computing device, the information relating to rate and depth of the chest compressions associated with the respective user of the respective mobile computing device to the remote server system, wherein sending the information relating to rate and depth of the chest compressions comprises sending the data structure to the remote server system;
analyze, by the remote server system, the information relating to rate and depth of the chest compressions associated with each respective user of each respective mobile computing device to determine a proficiency level of the respective user;
compare, by the remote server system, the proficiency level of each respective user to a proficiency standard required to be certified in life saving activities, wherein the proficiency standard required to be certified in life saving activities is set by medical guidelines in terms of rate and depth in a target range;
provide, by the server system, an indication of whether each respective user of each respective mobile computing device is ready for certification, wherein providing the indication comprises automatically sending an electronic certificate to a first mobile computing device of the plurality of mobile computing devices associated with a first user in response to the proficiency level of the first user meeting the proficiency standard; and
issue the certification for each respective user to a third party organization or a third party provider by the remote server system.

2. The system of claim 1, wherein each mobile computing device further comprises a display configured to provide a representation of the information relating to rate and depth of the chest compressions.

3. The system of claim 2, wherein the display of each respective mobile computing device is further configured to provide instructions regarding exercises to be completed by the respective user.

4. The system of claim 1, wherein the first mobile computing device displays, by a display of the first mobile computing device, the electronic certificate to the first user.

5. The system of claim 1, wherein the information relating to rate and depth of chest compressions is obtained by each mobile computing device under controlled test conditions.

6. The system of claim 5, wherein the controlled test conditions comprise having each respective user perform cardiopulmonary resuscitation (CPR) on a standard foam training pad or training dummy while the accelerometer of the respective mobile computing device measures motion.

7. The system of claim 6, wherein the controlled test conditions further comprise having each respective user answer quiz questions displayed on a display of the respective mobile computing device.

8. The system of claim 1, wherein each mobile computing device comprises at least one of a personal digital assistant, a cellular telephone, and a smartphone.

9. A method for certifying a user in life saving activities, the method comprising:
obtaining, with an accelerometer and a magnetometer of each respective mobile computing device of a plurality of mobile computing devices configured to be held by a respective user when the respective user is performing chest compressions, measurements of a vertical displacement of the hands of the respective user to determine information relating to rate and depth of the chest compressions and measurements of tilt of the respective mobile computing device, wherein raw accelerometer data from the accelerometer is received via an application programming interface (API) and double integrated and combined with tilt data from the magnetometer to measure the vertical displacement of each respective mobile computing device, and wherein determining the information relating to rate and depth of chest compressions comprises:
generating depth data associated with depths of chest compressions and rate data associated with rate of chest compressions based on the vertical displacement measured by double integrating the raw accelerometer data and the tilt data from the magnetometer; and
populating a data structure based on the depth data and the rate data;
associating, by a processor of each respective mobile computing device, the information relating to the rate and depth of the chest compressions with the respective user of the respective mobile computing device;
transmitting, by a communication interface of each respective mobile computing device, the information relating to rate and depth of the chest compressions associated with the respective user of the respective mobile computing device to a remote server system in direct communication with the plurality of mobile computing devices, wherein transmitting the information relating to rate and depth of the chest compressions comprises sending the data structure to the remote server system;
analyzing, by the remote server system, the information relating to rate and depth of the chest compressions associated with each respective user of each respective mobile computing device to determine a proficiency level of the respective user;
comparing, by the remote server system, the proficiency level of each respective user to a proficiency standard required to be certified in life saving activities, wherein the proficiency standard required to be certified in life saving activities is set by medical guidelines in terms of rate and depth in a target range;
providing, by the remote server system, an indication of whether each respective user of each respective mobile computing device is ready for certification, wherein providing the indication comprises automatically sending an electronic certificate to a first mobile computing device of the plurality of mobile computing devices associated with a first user in response to the proficiency level of the first user meeting the proficiency standard; and issuing, by the remote server system, the certification for each respective user to a third party organization or a third party provider.

10. The method of claim 9, wherein each mobile computing device further comprises a display configured to provide a representation of the information relating to rate and depth of the chest compressions.

11. The method of claim 10, wherein the display of each respective mobile computing device is further configured to provide instructions regarding exercises to be completed by the respective user.

12. The method of claim 10, further comprising displaying, by the display of the first mobile computing device, the electronic certificate to the first user.

13. The method of claim 9, wherein the information relating to rate and depth of chest compressions is obtained by each mobile computing device under controlled test conditions.

14. The method of claim 13, wherein the controlled test conditions comprise having each respective user perform cardiopulmonary resuscitation (CPR) on a standard foam training pad or training dummy while the accelerometer of the respective mobile computing device measures motion.

15. The method of claim 14, wherein the controlled test conditions further comprise having each respective user answer quiz questions displayed on a display of the respective mobile computing device.

16. The method of claim 9, wherein each mobile computing device comprises at least one of a personal digital assistant, a cellular telephone, and a smartphone.

17. The system of claim 1, wherein the system is further configured to access, by the remote server system, social networking contacts for each respective user of each respective mobile computing device and publish public recognition of the certification for each respective user to a social networking web site.

* * * * *